United States Patent
Govari et al.

(10) Patent No.: US 8,956,353 B2
(45) Date of Patent: Feb. 17, 2015

(54) ELECTRODE IRRIGATION USING MICRO-JETS

(75) Inventors: Assaf Govari, Haifa (IL); Athanassios Papaioannou, Los Angeles, CA (US)

(73) Assignee: Biosense Webster (Israel) Ltd. (IL)

( * ) Notice: Subject to any disclaimer, the term of this patent is extended or adjusted under 35 U.S.C. 154(b) by 660 days.

(21) Appl. No.: 13/339,782

(22) Filed: Dec. 29, 2011

(65) Prior Publication Data

US 2013/0172873 A1     Jul. 4, 2013

(51) Int. Cl.
*A61B 18/18*     (2006.01)

(52) U.S. Cl.
USPC ............................................ 606/41; 607/116

(58) Field of Classification Search
None
See application file for complete search history.

(56) References Cited

U.S. PATENT DOCUMENTS

| | | | |
|---|---|---|---|
| 5,807,395 | A | 9/1998 | Mulier et al. |
| 6,017,338 | A | 1/2000 | Brucker et al. |
| 6,210,411 | B1 | 4/2001 | Hofmann et al. |
| 6,226,542 | B1 | 5/2001 | Reisfeld |
| 6,301,496 | B1 | 10/2001 | Reisfeld |
| 6,814,733 | B2 | 11/2004 | Schwartz et al. |
| 6,892,091 | B1 | 5/2005 | Ben-Haim et al. |
| 6,997,924 | B2 | 2/2006 | Schwartz et al. |
| 7,156,816 | B2 | 1/2007 | Schwartz et al. |
| 7,536,218 | B2 | 5/2009 | Govari et al. |
| 7,537,595 | B2 | 5/2009 | McClurken |
| 2003/0163178 | A1 | 8/2003 | Davison et al. |
| 2007/0060832 | A1 | 3/2007 | Levin |
| 2008/0103494 | A1 | 5/2008 | Rioux et al. |
| 2008/0161795 | A1 | 7/2008 | Wang et al. |
| 2010/0030209 | A1 | 2/2010 | Govari et al. |
| 2010/0161795 | A1 | 6/2010 | Deridder et al. |
| 2010/0168548 | A1 | 7/2010 | Govari et al. |
| 2011/0276115 | A1* | 11/2011 | Merrill .......................... 607/106 |

FOREIGN PATENT DOCUMENTS

| | | |
|---|---|---|
| EP | 2 119 407 A1 | 11/2009 |
| EP | 2 145 596 A1 | 1/2010 |
| WO | WO 03/024349 A1 | 3/2003 |

OTHER PUBLICATIONS

European Search Report mailed on Mar. 15, 2013 from corresponding European Patent Application No. 12199705.0.

* cited by examiner

*Primary Examiner* — Brian T Gedeon
*Assistant Examiner* — Ankit Tejani

(57) ABSTRACT

A medical device includes an insertion tube, which has a distal end for insertion into a body of a subject, and a distal tip, which is fixed to the distal end of the insertion tube and is coupled to apply energy to tissue inside the body. The distal tip has an outer surface with a plurality of circumferentially distributed perforations formed therethrough. The perforations have diameters between 10 μm and 25 μm. A lumen passes through the insertion tube and delivers a cooling fluid to the tissue via the perforations.

12 Claims, 2 Drawing Sheets

ELECTRODE IRRIGATION USING MICRO-JETS

BACKGROUND OF THE INVENTION

1. Field of the Invention

This invention relates to medical devices. More particularly, this invention relates to cooling of tissue contacted by an invasive probe within the body.

2. Description of the Related Art

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in myocardial tissue associated with cardiac ganglionic plexi. In this condition, after unwanted signals are generated in the pulmonary veins or conducted through the pulmonary veins from other sources, they are conducted into the left atrium where they can initiate or continue arrhythmia.

Procedures for treating arrhythmia include disrupting the areas causing the arrhythmia by ablation, as well as disrupting the conducting pathway for such signals. Ablation of body tissue using electrical energy is known in the art. The ablation is typically performed by applying alternating currents, for example radiofrequency energy, to the electrodes, at a sufficient power to destroy target tissue. Typically, the electrodes are mounted on the distal tip of an invasive probe or catheter, which is inserted into a subject. The distal tip may be tracked in a number of different ways known in the art, for example by measuring magnetic fields generated at the distal tip by coils external to the subject.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

Previous approaches to controlling local heating include the inclusion of thermocouples within the electrode and feedback control, signal modulation, local cooling of the catheter tip, and fluid-assisted techniques, for example perfusion of the target tissue during the energy application, using chilled fluids. Typical of the last approach is Mulier, et al. U.S. Pat. No. 5,807,395.

Commonly assigned U.S. Pat. No. 6,997,924, which is herein incorporated by reference, describes a technique of limiting heat generated during ablation by determining a measured temperature of the tissue and a measured power level of the transmitted energy, and controlling the power output level responsively to a function of the measured temperature and the measured power level.

More recently, commonly assigned U.S. Patent Application Publication No. 2010/0030209 by Govari et al., which is herein incorporated by reference, describes an insertion tube, having an outer surface with a plurality of perforations through the outer surface, which are typically about 100 μm in diameter, and are distributed circumferentially and longitudinally over the distal tip. A lumen passes through the insertion tube and is coupled to deliver a fluid to the tissue via the perforations.

SUMMARY OF THE INVENTION

There is provided according to embodiments of the invention a medical device, including an insertion tube, which has a distal end for insertion into a body of a subject, and a distal tip, which is fixed to the distal end of the insertion tube and is coupled to apply energy to tissue inside the body. The distal tip has an outer surface with a plurality of circumferentially distributed perforations formed therethrough. The perforations have diameters between 10 μm and 25 μm. A lumen passes through the insertion tube and delivers a cooling fluid to the tissue via the perforations There may be at least eight perforations.

According to an additional aspect of the device, there may be at least fifty perforations.

According to another aspect of the device, the outer surface of the distal tip includes a conductive material, which is configured to contact and apply electrical energy to the tissue so as to ablate the tissue.

There is provided according to embodiments of the invention a medical apparatus, including an elongate probe, for insertion into a body of a subject, the probe including an insertion tube having a distal end for engagement with a target tissue in the body. A distal tip, which is fixed to the distal end of the insertion tube, is coupled to apply energy to the tissue inside the body, and has an outer surface with a plurality of perforations formed therethrough. The perforations are distributed circumferentially and longitudinally over the distal tip and have diameters between 10 μm and 25 μm. A lumen passing through the insertion tube delivers a fluid to the tissue via the perforations. The apparatus includes an energy generator for supplying the energy to the distal tip, and an irrigation pump to supply the fluid via the lumen and the perforations to the tissue.

According to aspect of the apparatus, the outer surface of the distal tip includes a conductive material and is configured to contact the tissue, and wherein the energy generator is coupled to supply electrical energy to the distal tip in order to ablate the tissue.

According to a further aspect of the apparatus, the elongate probe is configured for insertion through a blood vessel into a heart of the subject for ablation of myocardial tissue in the heart.

Other aspects of the invention provide methods that are carried out by the medical device and apparatus.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

System Description

Figure 1:
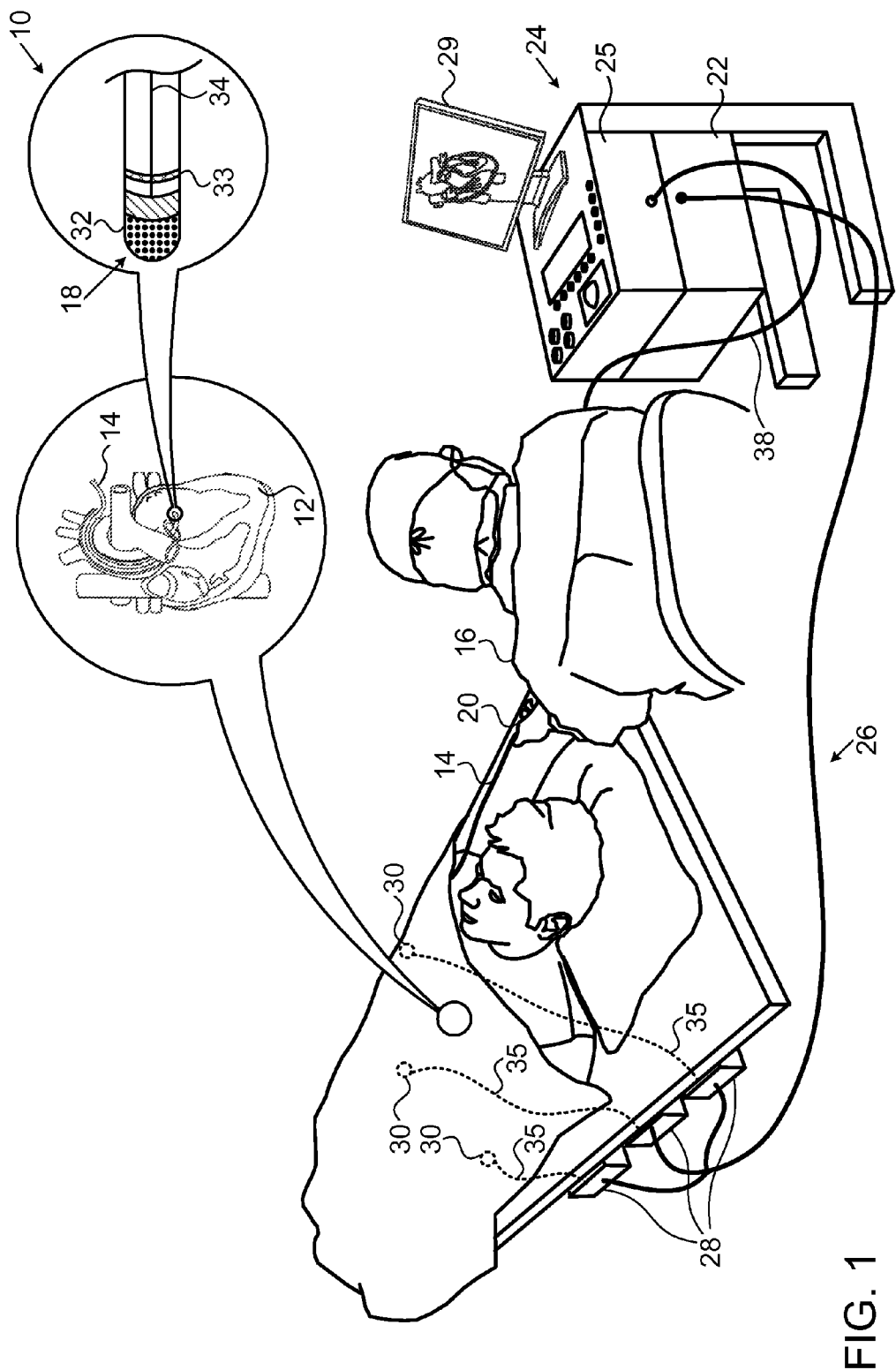
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through an ablation electrode 32 located at or near the distal tip 18 via cables 34 and 38 to the console 24. While a single ablation electrode 32 is shown, more than one can be present. Pacing signals and other control signals may be conveyed from the console 24 through the cables 34 and 38 and the ablation electrode 32 to the heart 12. Sensing electrodes 33, also connected to the console 24 are typically disposed near the ablation electrode 32 and have connections to the cables 34 and 38.

Wire connections 35 link the console 24 with body surface electrodes 30 and other components of a positioning subsystem. A temperature sensor (not shown), typically a thermocouple or thermistor, may be mounted on or near the ablation electrode 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning system 26 of the system 10 that measures location and orientation coordinates of the catheter 14.

In one embodiment, the positioning system 26 comprises a magnetic position tracking arrangement that determines the position and orientation of the catheter 14 by generating magnetic fields in a predefined working volume its vicinity and sensing these fields at the catheter using field generating coils 28 and may include impedance measurement, as taught, for example in U.S. Patent Application Publication No. 2007/0060832, which is herein incorporated by reference. The positioning system 26 may be enhanced by position measurements using the impedance measurements described in the above-noted U.S. Pat. No. 7,536,218.

As noted above, the catheter 14 is coupled to the console 24 by cable 38, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system 26 to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Figure 2:
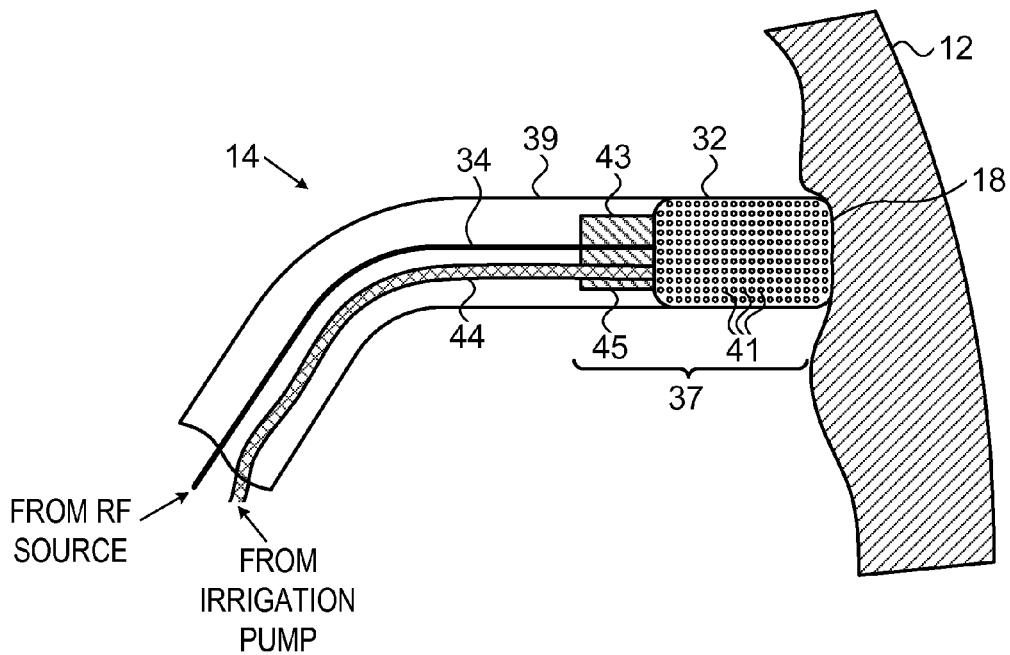
FIG. 2, which is a schematic sectional view of the distal end of catheter in engagement with endocardial tissue in accordance with an embodiment of the invention.

Reference is now made to FIG. 2, which is a schematic sectional view of distal end 37 of catheter 14 in engagement with endocardial tissue in heart 12, in accordance with an embodiment of the invention. The ablation electrode 32, disposed at the distal tip 18, is fixed to the distal end of an insertion tube 39 of the catheter 14. The ablation electrode 32 typically comprises a conductive material, such as platinum, while the insertion tube 39 has an insulating flexible outer sheath. The outer surface of the ablation electrode 32 is penetrated by multiple perforations 41, which are distributed over the surface of the ablation electrode 32 both longitudinally (i.e., along the direction parallel to the longitudinal axis of the catheter 14) and circumferentially (along circumferences around the axis). The cables 34 and 38 convey RF energy from the ablation power generator 25 (FIG. 1) to the ablation electrode 32, which delivers the energy to the endocardial surface of the heart 12 in order to ablate the underlying tissue.

The proximal end of the distal tip 18 is closed off by a plug 43, which has a fluid inlet 45 feeding the interior space of the ablation electrode 32. A lumen 44 passing through the insertion tube 39 conveys irrigation fluid to the fluid inlet 45, the irrigation fluid filling the interior space of the ablation electrode 32. The fluid exits the ablation electrode 32 through the perforations 41 to cool the distal tip 18 and the contacted myocardial tissue.

Figure 3:
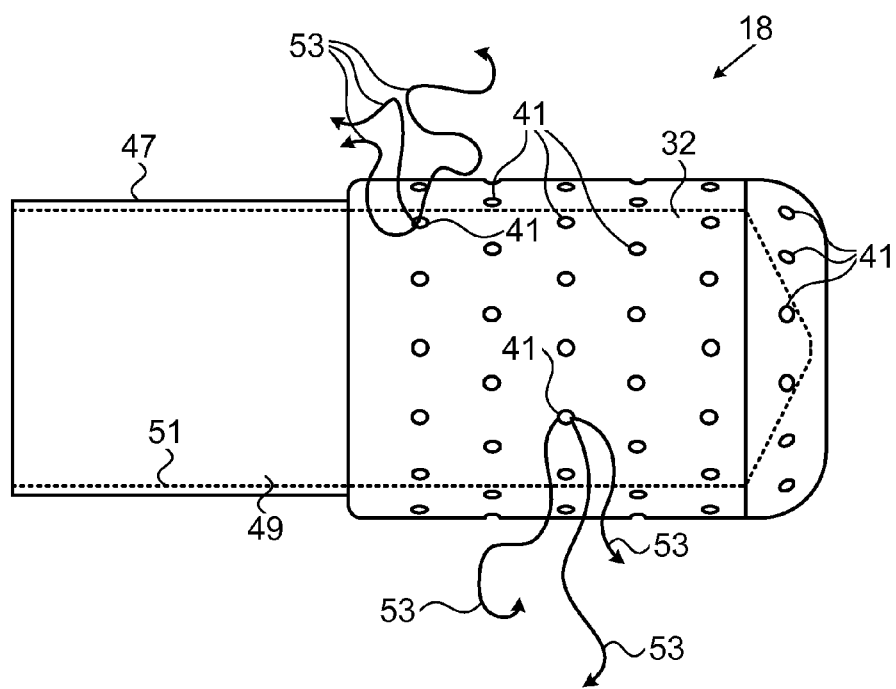
FIG. 3 is a schematic side view of the distal tip of the catheter shown in FIG. 2, showing details of the perforations, in accordance with an embodiment of the invention.

Reference is now made to FIG. 3, which is a schematic side view of the distal tip 18 and the ablation electrode 32, showing details of the perforations 41 in accordance with an embodiment of the invention. The distal tip 18 and the ablation electrode 32 are hollow, with an outer surface 47 that encloses an interior space 49 (shown bounded by a broken line 51 in FIG. 3).

The perforations 41 extend from the perforations 41 into the interior space 49. For cardiac ablation applications, the distal tip 18 shown in FIG. 3 is typically about 2.5 mm in diameter and 6 mm long, with a wall thickness in the distal part of the tip of about 0.25 mm. These dimensions, however, are given solely by way of illustration, and larger or smaller dimensions may be used depending on application requirements. The edges of the ablation electrode 32, at both its distal and proximal extremities, are typically rounded in order to avoid possible concentration of the RF electric field around the edges. The ablation electrode 32 may be surfaced with a gold film in order to enhance heat conduction. Typically, the perforations 41 are formed in the ablation electrode 32 itself, as shown in FIG. 3. However this is not essential. The perforations could be formed in the outer surface 47. For example, the perforations could be interleaved between a plurality of ablation electrodes. The perforations 41 may be produced by creating an electrical discharge between a needle electrode and the ablation electrode 32, as taught in the above-noted U.S. Patent Application Publication No. 2010/0030209.

The ablation electrode 32 should have at least eight perforations in order to distribute the irrigation over the tip both longitudinally and circumferentially without overloading the heart with the cooling fluid. It is advantageous, however, to have at least fifty perforations in the distal tip. A current embodiment features 96 perforations.

The above-noted U.S. Patent Application Publication No. 2010/0030209 describes perforations in a conductive catheter tip with diameters no greater than 0.2 mm, and typically with diameters of approximately 0.1 mm. The inventors have found that perforations of even smaller diameter (10-25 µm) are particularly effective for purposes of irrigation. It is believed that perforations of this order in size create turbulence in the emitted fluid streams, creating turbulent diffusion such as eddies and vortices along the outer surfaces of the distal tip 18 and the target tissue of the heart 12. The turbulence tends to homogenize the fluid flowing over the ablation electrode and over the ablated area and thus provides better, more uniform cooling. This result is unexpected, as the use of such small apertures was thought to be less effective than a comparable number of larger perforations, as a smaller volume of irrigation fluid should reach the target tissue and the ablation electrode. The perforations need not be uniform in diameter, so long as the diameters are small enough so that turbulent flow can be feasibly achieved.

The irrigation fluid pressure should be about 15 psi in order to generate the desired degree of turbulent flow, which is represented by irregularly curved lines 53 originating from perforations 41. This value may vary according to the distribution of diameters of the perforations 41, so long as the pressure is sufficient to generate turbulent flow through each of them.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:
1. A medical device, comprising:
an insertion tube, having a distal end for insertion into a body of a subject;
a distal tip, which is fixed to the distal end of the insertion tube and is coupled to apply energy to tissue inside the body, and which has an outer surface with a plurality of perforations formed therethrough, the perforations being distributed circumferentially and longitudinally over the distal tip and having diameters between 10 µm and 25 µm; and
a lumen passing through the insertion tube and coupled to deliver a fluid to the tissue via the perforations.
2. The device according to claim 1, wherein the plurality of perforations comprises at least eight perforations.
3. The device according to claim 2, wherein the plurality of perforations comprises at least fifty perforations.
4. The device according to claim 1, wherein the outer surface of the distal tip comprises a conductive material, which is configured to contact and apply electrical energy to the tissue so as to ablate the tissue.
5. A medical apparatus, comprising:
an elongate probe, for insertion into a body of a subject, the probe comprising:
an insertion tube, having a distal end for engagement with a target tissue in the body;
a distal tip, which is fixed to the distal end of the insertion tube and is coupled to apply energy to the tissue inside the body, and which has an outer surface with a plurality of perforations formed therethrough, the perforations being distributed circumferentially and longitudinally over the distal tip and having diameters between 10 µm and 25 µm;
a lumen passing through the insertion tube and coupled to deliver a fluid to the tissue via the perforations;
an energy generator, for coupling to the probe so as to supply the energy to the distal tip; and
an irrigation pump, for coupling to the lumen so as to supply the fluid via the lumen and the perforations to the tissue.
6. The apparatus according to claim 5, wherein the outer surface of the distal tip comprises a conductive material and is configured to contact the tissue, and wherein the energy generator is coupled to supply electrical energy to the distal tip in order to ablate the tissue.
7. The apparatus according to claim 5, wherein the elongate probe is configured for insertion through a blood vessel into a heart of the subject for ablation of myocardial tissue in the heart.
8. A method for treatment, comprising:
inserting an elongate probe into a body of a subject, the elongate probe comprising:
an insertion tube, having a distal end for insertion into the body;
a distal tip, which is fixed to the distal end of the insertion tube and is coupled to apply energy to a tissue inside the body, and which has an outer surface with a plurality of perforations formed therethrough, the perforations being distributed circumferentially and longitudinally over the distal tip and having diameters between 10 μm and 25 μm;

a lumen passing through the insertion tube and in fluid communication with the perforations;

applying energy through the distal tip to tissue inside the body; and supplying a fluid via the lumen and the perforations to the tissue.

9. The method according to claim 8, wherein supplying the fluid comprises cooling the distal tip and the tissue.

10. The method according to claim 8, wherein supplying the fluid comprises emitting a turbulent flow of the fluid from the perforations that flows about the tissue and the distal tip.

11. The method according to claim 8, wherein supplying the fluid comprises generating a fluid pressure of the fluid within the insertion tube of 15 psi.

12. The method according to claim 8, wherein inserting the elongate probe comprises inserting the elongate probe through a blood vessel into a heart of the subject, and wherein applying energy comprises ablating myocardial tissue in the heart.

* * * * *